United States Patent [19]

Sawchuk et al.

[11] Patent Number: 5,759,197
[45] Date of Patent: Jun. 2, 1998

[54] PROTECTIVE FEEDTHROUGH

[75] Inventors: Robert T. Sawchuk, White Bear Lake; Lynn M. Seifried, Minneapolis, both of Minn.; Bill Simmons, Chandler, Ariz.; Jeff Galvin; David Ruben, both of Mesa, Ariz.

[73] Assignee: Medtronic, Inc., Minneapolis, Minn.

[21] Appl. No.: 550,273

[22] Filed: Oct. 30, 1995

Related U.S. Application Data

[63] Continuation of Ser. No. 317,507, Oct. 4, 1994, abandoned.

[51] Int. Cl.⁶ .................. A61N 1/375; H01B 17/30
[52] U.S. Cl. .................. 607/36; 607/37; 174/50.61
[58] Field of Search .................. 607/36–38; 174/50.61; 361/302; 333/158, 182–185

[56] References Cited

U.S. PATENT DOCUMENTS

| | | |
|---|---|---|
| 1,180,614 | 4/1916 | Simpson. |
| 2,756,375 | 7/1956 | Peck. |
| 3,235,939 | 2/1966 | Rodriguez et al. |
| 3,266,121 | 8/1966 | Rayburn. |
| 3,304,362 | 2/1967 | August. |
| 3,538,464 | 11/1970 | Walsh. |
| 3,546,638 | 12/1970 | Park. |
| 3,624,460 | 11/1971 | Correll ............... 317/230 |
| 3,844,921 | 10/1974 | Benedict ............... 204/196 |
| 3,920,888 | 11/1975 | Barr ............... 174/152 GM |
| 3,945,387 | 3/1976 | Adams. |
| 3,961,295 | 6/1976 | Hollyday. |
| 3,968,802 | 7/1976 | Ballis. |
| 4,010,759 | 3/1977 | Boer ............... 128/419 P |
| 4,015,175 | 3/1977 | Kendall et al. ............... 361/313 |
| 4,038,990 | 8/1977 | Thompson. |
| 4,041,587 | 8/1977 | Kraus ............... 29/25.42 |
| 4,056,105 | 11/1977 | Ravas. |
| 4,059,116 | 11/1977 | Adams. |
| 4,079,343 | 3/1978 | Nijman. |
| 4,083,022 | 4/1978 | Kijman ............... 333/79 |
| 4,107,762 | 8/1978 | Shim et al. ............... 361/433 |
| 4,144,509 | 3/1979 | Boutros. |
| 4,148,003 | 4/1979 | Colburn et al. ............... 333/181 |
| 4,152,540 | 5/1979 | Duncan et al. ............... 174/152 |
| 4,168,351 | 9/1979 | Taylor ............... 429/48 |
| 4,187,481 | 2/1980 | Boutros. |
| 4,220,813 | 9/1980 | Kyle ............... 174/152 |
| 4,222,626 | 9/1980 | Hollyday. |
| 4,247,881 | 1/1981 | Coleman ............... 361/302 |
| 4,314,213 | 2/1982 | Wakino ............... 333/182 |
| 4,320,763 | 3/1982 | Money. |
| 4,328,807 | 5/1982 | Jirak. |
| 4,333,470 | 6/1982 | Barthel. |
| 4,352,951 | 10/1982 | Kyle. |

(List continued on next page.)

FOREIGN PATENT DOCUMENTS

| | | | |
|---|---|---|---|
| 0 331 959 A2 | 2/1989 | European Pat. Off. ....... A61N 1/375 |
| 0331959 | 9/1989 | European Pat. Off. . |
| 0623363 | 11/1994 | European Pat. Off. . |
| 28 15 118 A1 | of 0000 | Germany ............... H01G 4/42 |

*Primary Examiner*—John P. Lacyk
*Assistant Examiner*—Stephen Huang
*Attorney, Agent, or Firm*—Thomas F. Woods; Daniel W. Latham; Harold R. Patton

[57] ABSTRACT

A feedthrough configuration for a hermetically sealed implantable medical device includes a metal case having an aperture and a feedthrough in the aperture which includes a ferrule sealed in the aperture, a pin extending through the ferrule and the aperture, an insulating material supporting the pin within the ferrule and an electrically conductive block spaced from the ferrule and in electrical connection with the pin. A device for electrical or electromagnetic protection can be connected to a peripheral upstanding portion of the ferrule and a peripheral skirt portion of the block. This arrangement of feedthrough elements can be particularly useful if the protective device is a chip capacitor which typically has a flat-sided configuration that can bridge the space between the ferrule and the block and be connected at one end to the block and at the other end to the ferrule.

12 Claims, 4 Drawing Sheets

U.S. PATENT DOCUMENTS

| | | | |
|---|---|---|---|
| 4,362,792 | 12/1982 | Bowsky et al. | 429/181 |
| 4,421,947 | 12/1983 | Kyle . | |
| 4,424,551 | 1/1984 | Stevenson . | |
| 4,456,786 | 6/1984 | Kyle . | |
| 4,500,159 | 2/1985 | Briones . | |
| 4,556,613 | 12/1985 | Taylor et al. | 429/101 |
| 4,616,655 | 10/1986 | Weinberg . | |
| 4,660,907 | 4/1987 | Belter . | |
| 4,678,868 | 7/1987 | Kraska . | |
| 4,683,516 | 7/1987 | Miller | 361/328 |
| 4,694,265 | 9/1987 | Kupper . | |
| 4,737,601 | 4/1988 | Gartzke | 174/152 |
| 4,741,710 | 5/1988 | Hogan et al. | 439/620 |
| 4,745,923 | 5/1988 | Winstrom . | |
| 4,750,495 | 6/1988 | Moore . | |
| 4,791,391 | 12/1988 | Linnell et al. | 333/184 |
| 4,796,630 | 1/1989 | Regna . | |
| 4,903,701 | 2/1990 | Moore . | |
| 4,934,366 | 6/1990 | Truex et al. | 128/419 P |
| 5,032,692 | 7/1991 | DeVolder | 174/52.3 |
| 5,057,041 | 10/1991 | Yu et al. . | |
| 5,070,605 | 12/1991 | Daglow et al. | 29/842 |
| 5,104,755 | 4/1992 | Taylor et al. | 429/181 |
| 5,144,946 | 9/1992 | Weinberg et al. | 178/419 P |
| 5,170,806 | 12/1992 | Colen . | |
| 5,184,285 | 2/1993 | Murphy . | |
| 5,213,522 | 5/1993 | Kojima . | |
| 5,246,389 | 9/1993 | Briones . | |
| 5,333,095 | 7/1994 | Stevenson et al. | 361/302 |
| 5,336,253 | 8/1994 | Gordon . | |
| 5,406,444 | 4/1995 | Selfried . | |
| 5,440,447 | 8/1995 | Shipman et al. . | |
| 5,531,003 | 7/1996 | Seifried et al. . | |
| 5,535,097 | 7/1996 | Ruben et al. | 361/736 |
| 5,620,476 | 4/1997 | Truex et al. | 607/36 |
| 5,650,759 | 7/1997 | Hittman et al. | 333/182 |

PROTECTIVE FEEDTHROUGH

This application is a continuation of application Ser. No. 08/317,507 filed on Oct. 4, 1994, now abandoned.

BACKGROUND OF THE INVENTION

This invention relates generally to electrical medical devices and, more particularly, to feedthroughs for hermetically sealed electrical connections which provide electrical or EMI (electromagnetic interference) protection for such devices.

Implantable medical devices typically have a metal case and a connector block mounted to the metal case which includes receptacles for leads which may be used for electrical stimulation or sensing of physiological signals. Hermetically sealed within the case are the battery and the circuitry. To connect the leads outside the metal case with the circuitry and the battery inside the metal case, electrical feedthroughs are employed.

Electrical feedthroughs serve the purpose of providing an electrical circuit path extending from the interior of a hermetically sealed container to an external point outside the container while maintaining the hermetic seal of the container. The conductive path is provided through the feedthrough by a conductor pin which is electrically insulated from the container itself. Such feedthroughs typically include a ferrule which permits attachment of the feedthrough to the case, a conductor pin or lead and a hermetic glass or ceramic seal which supports the pin within the ferrule. One such feedthrough is that disclosed in U.S. Pat. No. 4,678,868 issued to Kraska et al in which a brazed alumina insulator provides hermetic sealing and electrical isolation of a niobium conductor pin from the case. Such feedthroughs are typically used in implantable pulse generators (IPG's) such as heart pacemakers or neurostimulators.

It has been discovered that such electrical devices can, under some circumstances, be susceptible to electromagnetic interference (EMI) such that its functioning is impaired. In particular, it has been found that EMI at specific frequencies can inhibit pacing in a heart pacemaker IPG and/or cause fast or erratic pacing. This problem can be addressed by incorporating a capacitor structure within the feedthrough ferrule thus shunting any EMI at the entrance to the IPG for high frequencies. A feedthrough/capacitor which can be used for such purposes is disclosed in U.S. Pat. No. 4,424,551 issued to Stephenson et al or in co-pending U.S. patent application Ser. No. 08/038,373 which places a toroidal capacitor directly into the feedthrough ferrule and around the pin with the capacitor electrically contacting the pin and the ferrule. However, such feedthrough/capacitors require many production steps and close tolerances and are therefore expensive and time consuming to manufacture.

In addition to the EMI which can cause malfunction of implantable medical devices, such medical devices also require protection against electrical interference from electrocautery and defibrillation pulses which can damage the circuitry of such devices. Such protection is typically provided by means of one or more zener diodes which are connected between the circuit to be protected and the case (or an indifferent electrode) in a manner which grounds voltage and current surges through the diode. The use of such diodes is disclosed in greater detail in U.S. Pat. Nos. 4,320,763; 4,328,807; 4,333,470; 4,745,923; 4,750,495; and 4,796,630. However, it would be desirable to provide a feedthrough which could be adapted to provide protection against this and other forms of electrical and electromagnetic interference.

It is therefore an object of the present invention to provide a feedthrough which effectively protects against interference from electrical or electromagnetic sources.

It is also an object of the present invention to provide a feedthrough adapted to include a variety of protective devices.

It is also an object of the present invention to provide a feedthrough suitable for low cost production.

SUMMARY OF THE INVENTION

These and other objects have been accomplished by the protective feedthrough of the present invention. We have discovered a feedthrough configuration for a hermetically sealed implantable medical device which includes a metal case having an aperture and a feedthrough in the aperture which includes a ferrule sealed in the aperture, a pin extending through the ferrule and the aperture, an insulating material supporting the pin within the ferrule and an electrically conductive block spaced from the ferrule and in electrical connection with the pin. A device for electrical or electromagnetic protection can be connected to a peripheral upstanding portion of the ferrule and a peripheral skirt portion of the block. This arrangement of feedthrough elements can be particularly useful if the protective device is a chip capacitor which typically has a flat-sided configuration that can bridge the space between the ferrule and the block and can be connected at one end to the block and at the other end to the ferrule. This works especially well if the peripheral skirt of the block is in a good linear alignment with the upstanding peripheral portion of the ferrule.

In a preferred embodiment of the invention, the block has a flat top surface which allows the feedthrough to be connected with a separate electrical circuit of the medical device by a lead extending from the electrical circuit which is connected by wire bonding, welding or soldering to the top of the block.

In another preferred embodiment of the invention, additional chip capacitors are connected between the block and ferrule in spaced relation around the feedthrough in order to provide increased EMI protection. Typically, between two and four capacitors can be used. If two capacitors are used, they can be arranged on opposite sides of the feedthrough. When such feedthroughs are used in a linear array in the case, the capacitors can be offset from the linear axis to provide a compact feedthrough arrangement.

DETAILED DESCRIPTION OF THE INVENTION

Figure 1:
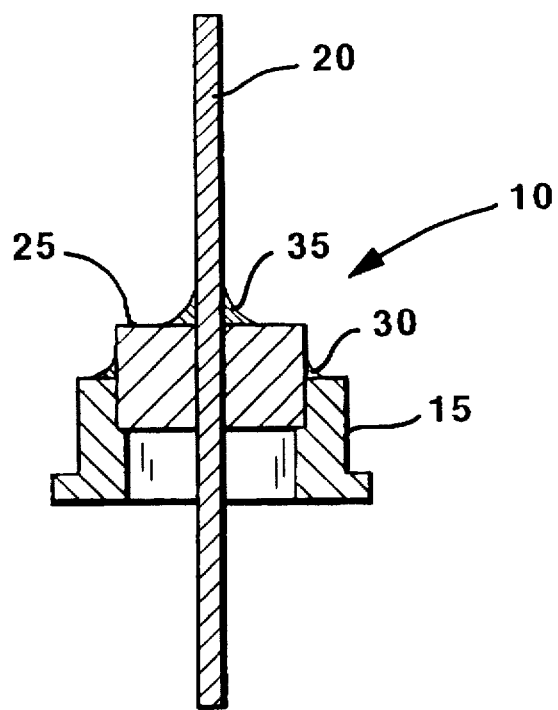
FIG. 1 is a cross-sectional view of a conventional feedthrough for an implantable medal device.
Figure 2:
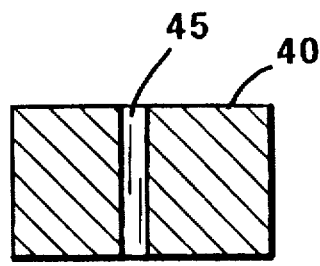
FIG. 2 is a cross-sectional view of an electrically conductive block used in the invention.
Figure 3:
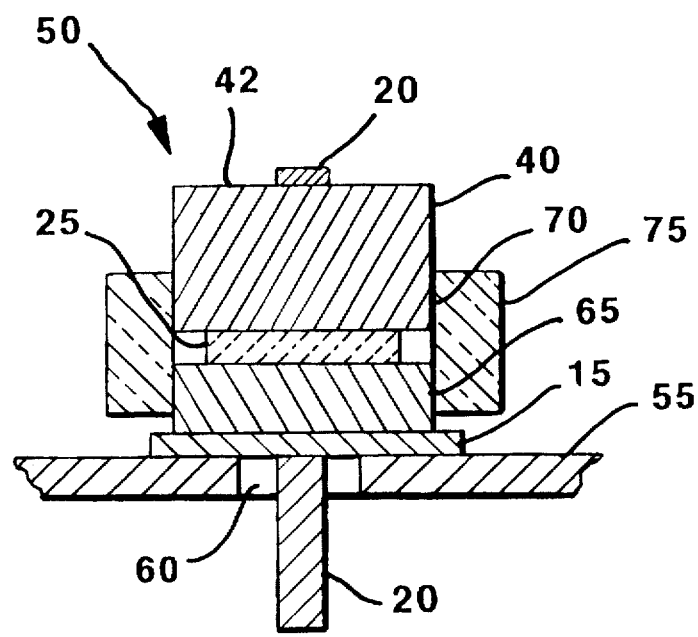
FIG. 3 is an elevational view of a feedthrough according to the invention.
Figure 4:
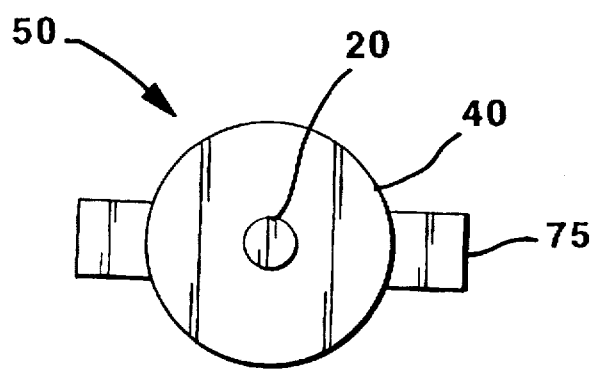
FIG. 4 is a top plan view of the feedthrough of FIG. 3.

The present invention relates to a feedthrough for a hermetically sealed implantable medical device. Such devices include a metal case of conventional design having an aperture containing a feedthrough. A durable metal case for an implantable medical device can be made of titanium or a titanium alloy. In the prior art, a suitable feedthrough for such a device is the brazed alumina feedthrough set forth in U.S. Pat. No. 4,678,868 issued to Kraska et al which is incorporated herein in its entirety. A similar feedthrough 10 is shown in FIG. 1 in which a ferrule 15 is disposed around a pin 20 which is supported by an insulator 25. The insulator 25 is secured to the ferrule 15 by means of a braze joint 30. Similarly, the pin 20 is secured to the insulator 25 by means of a braze joint 35. A feedthrough according to the present invention can be made from the feedthrough 10 of FIG. 1 by adding a block 40 as shown in FIG. 2 which has an aperture 45 adapted to accept the pin 20 of the feedthrough 10 of FIG. 1. The block 40 is made from an electrically conductive material that is solderable or weldable or may be wire-bonded to leads from the circuitry components of the device. For example, niobium or nickel would be satisfactory block materials. Preferably, the block 40 has a flat top portion 42 which allows electrical connections to be readily made to that portion of the block 40. The pin 20 can then be brazed, soldered or otherwise electrically attached to the block 40 and, if necessary, any excess length of the pin 20 can then be removed. FIGS. 3 and 4 show this feedthrough construction more clearly with the block 40 seated against the insulator 25 such that it is spaced from the ferrule 15 by the insulator 25. The resulting feedthrough 50 is in sealing engagement with one side of the case 55 while the pin 20 projects through an aperture 60 in the case 55. Typically, the ferrule 15 is sealed to the case by welding. In this arrangement, the ferrule 15 is shown to have a peripheral portion 65 which is upstanding from the surface of the case 55 while the block has a peripheral skirt portion 70 adjacent to the upstanding peripheral portion 65 of the ferrule and in linear alignment with the peripheral portion 65 of the ferrule. A device for electrical or electromagnetic protection 75 is electrically connected to the peripheral portion 65 of the ferrule 15 and also electrically connected to the peripheral skirt portion 70 of the block 40.

Figure 5:
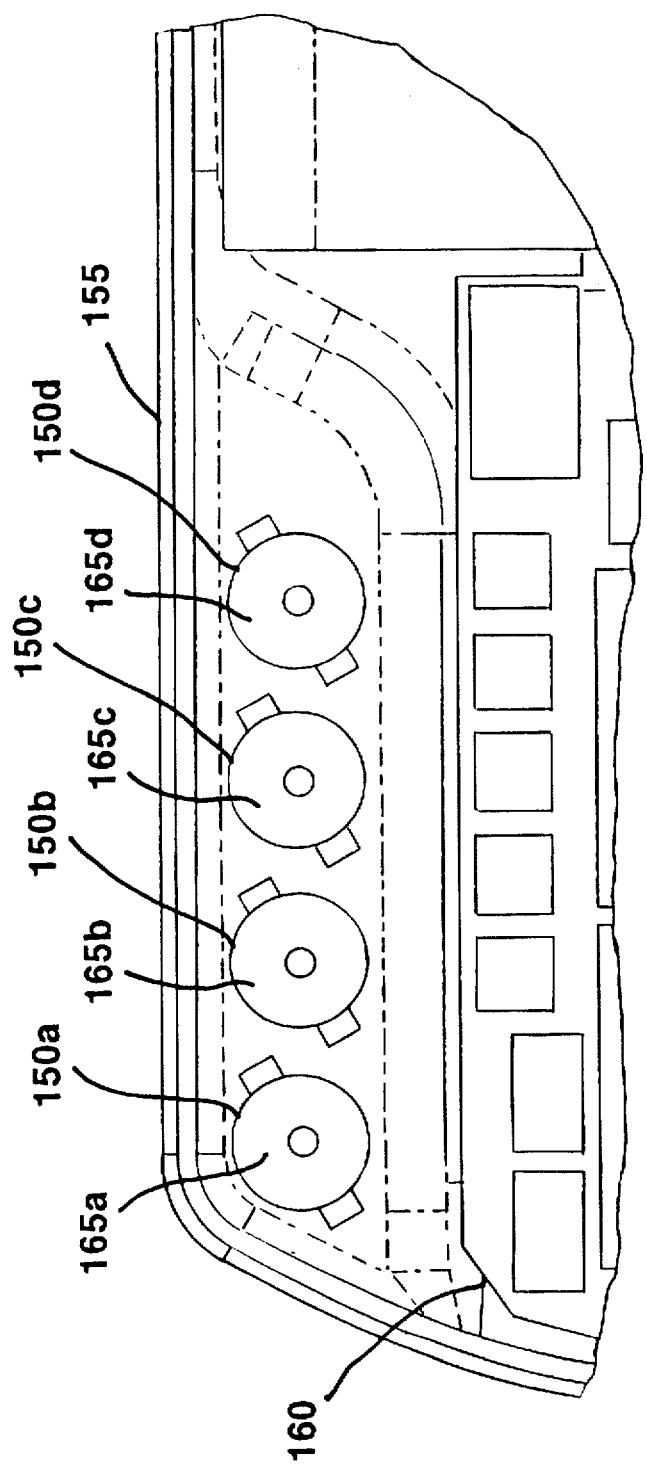
FIG. 5 is a partial plan view of a case assembly for an implantable medical device with included feedthrough array and circuitry.

FIG. 5 shows a linear array of feedthroughs 150a–d mounted in a case 155. A hybrid circuit assembly 160 is also mounted in the case 155 with their conductive block portions 165a–d spaced apart from the circuit assembly 160. Connections can be made from the circuit assembly 160 to the individual feedthroughs 150a–d by means of conventional electrical conductor materials affixed to the block portions 165a–d. Preferably, the block portions 165a–d have flat top portions to provide a surface for easy connections with electrical conductors.

One preferred device for electrical or electromagnetic protection in the present invention is a capacitor such as a chip capacitor which can be incorporated with the feedthrough as shown in FIGS. 3 and 4. Such chip capacitors can be attached at each end to the block and ferrule elements of the feedthrough by the use of a conductive epoxy adhesive. Other methods of attachment, such as soldering, are also acceptable. Preferably, more than one chip capacitor is used in order to provide improved EMI protection. Two, three or even four chip capacitors can be used as needed. When used in a linear array of feedthroughs as shown in FIG. 5, the array can be provided in a compact form by orienting the feedthroughs such that the chip capacitors are offset from the linear axis of the array. Feedthroughs provided with chip capacitors with combined capacitances in the range of about 1–4 nF were tested for insertion loss performance in various capacitor configurations with the average results set forth in Table 1.

TABLE 1

| Capacitor Configuration | Average Insertion Loss Performance (db) | | | |
| --- | --- | --- | --- | --- |
| | 3.5 MHz | 28.5 MHz | 450 MHz | 2540 MHz |
| 1-1nF | −2.0 | −12.5 | −26.4 | −20.0 |
| 2-1nF at 180° | −3.6 | −17.0 | −32.1 | −26.1 |
| 3-1nF at 90° | −5.9 | −20.7 | −35.6 | −33.7 |
| 4-1nF at 90° | −7.4 | −20.8 | −36.5 | −35.0 |
| 2-2nF at 180° | −8.6 | −20.6 | −24.6 | −30.8 |

Figure 6:
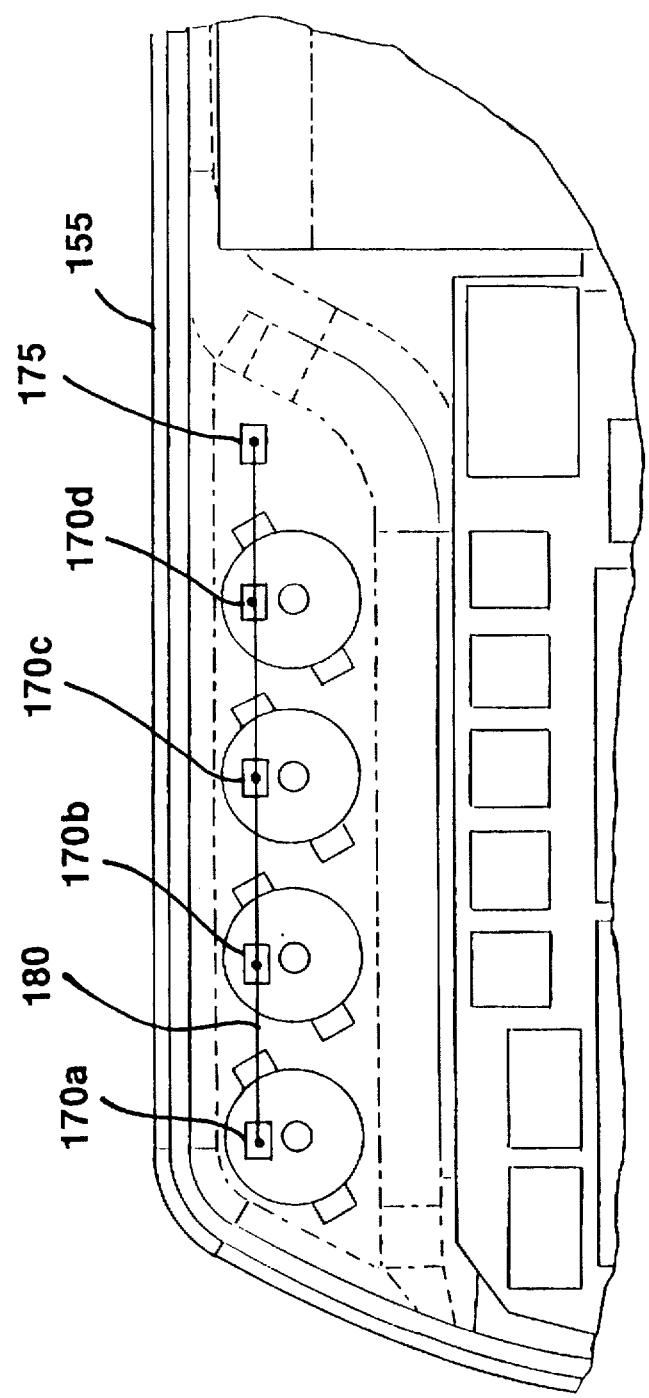
FIG. 6 is a partial plan view of a case assembly for an implantable medical device with included feedthrough array, zener diode array and circuitry.

In yet another application of protective devices to the feedthrough, protective devices can also be added to the block portion of the feedthrough as shown in FIG. 6. FIG. 6 shows single case zener diodes 170a–d (e.g. 0.38"×0.38" 10 V zener diodes) employed to provide protection against excessive voltage. The diodes 170a–d can be attached on one surface to the block portion of the feedthrough and on a second surface to a wire conductor 180 which joins the diodes 170a–d on the feedthrough array. These connections can be made by any suitable means for making electrical connections such as by soldering or conductive epoxy. The conductor 180 also extends to a similar diode 175 which has been electrically connected to the conductor 180 on one side and to the case 155 on a second side. The diodes thereby form the conventional back-to-back arrangement which break down at a predetermined voltage to provide protection against excessive voltage.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A hermetically sealed implantable medical device, comprising:
   (a) a metal case having an interior surface and an exterior surface and an aperture extending between the interior and exterior surfaces; and
   (b) a feedthrough disposed in the case aperture, comprising:
      (1) an electrically conductive ferrule disposed in the case aperture and in sealing engagement therewith, the ferrule having a first outer peripheral surface upstanding from one of the case surfaces;
      (2) an electrically conductive pin extending through the ferrule and the aperture such that the pin has a first end projecting from the exterior surface of the case and a second end projecting from the interior surface of the case;
      (3) an insulating material supporting the pin within the ferrule and in sealing engagement with the ferrule and with the pin;
      (4) a preformed electrically conductive block spaced from the ferrule and in electrical connection with the pin, the block having a second outer peripheral surface substantially in alignment with the first outer peripheral surface of the ferrule, wherein the conductive block is spaced from the ferrule by the insulating material; and
      (5) a device for electrical or electromagnetic protection electrically connected at and mounted to a first point on the first outer peripheral surface of the ferrule and electrically connected at and mounted to a second point on the second outer peripheral surface of the block.

2. A medical device according to claim 1 wherein the electrically conductive block has a flat top surface.

3. A medical device according to claim 2 also comprising an electrical circuit spaced apart from the conductive block and a conductor extending from the electrical circuit and electrically connected to the top of the conductive block.

4. A medical device according to claim 1 wherein the device for electrical or electromagnetic protection comprises a capacitor.

5. A hermetically sealed implantable medical device, comprising:
   (a) a metal case having an interior surface and an exterior surface and an aperture extending between the interior and exterior surfaces; and
   (b) a feedthrough in the case aperture comprising:
      (1) an electrically conductive ferrule at the case aperture in sealing engagement with the case, the ferrule having a having a first outer peripheral surface upstanding from one of the case surfaces;
      (2) an electrically conductive pin extending through the ferrule and the aperture such that the pin has a first end projecting from the exterior surface of the case and a second end projecting from the interior surface of the case;
      (3) an insulating material supporting the pin within the ferrule and in sealing engagement with the ferrule and with the pin;
      (4) a preformed electrically conductive block spaced from the ferrule and in electrical connection with the pin, the block having a second outer peripheral surface substantially in alignment with the first outer peripheral surface of the ferrule.
      (5) a first device for electrical or electromagnetic protection electrically connected at and mounted to a first point on the first outer peripheral surface of the ferrule and electrically connected at and mounted to a second point on the second outer peripheral surface of the block, and:
      (6) a second device for electrical or electromagnetic protection electrically connected at and mounted to a third point on the first outer peripheral surface of the ferrule and electrically connected at and mounted to a fourth point on the second outer peripheral surface of the block, the third and fourth points being disposed on opposite sides of the ferrule and block, respectively, from those of the first and second points.

6. A medical device according to claim 5, wherein the feedthrough is one of an array of similar feedthroughs, the array defining a linear axis, the first and second electrical and electromagnetic protection devices being disposed at locations offset from the linear axis.

7. A hermetically sealed implantable medical device, comprising:
   (a) a metal case having an interior surface and an exterior surface and an aperture extending between the interior and exterior surfaces;
   (b) a feedthrough in the case aperture comprising:
      (1) an electrically conductive ferrule at the case aperture in sealing engagement with the case;
      (2) an electrically conductive pin extending through the ferrule and the aperture such that the pin has a first end projecting from the exterior surface of the case and a second end projecting from the interior surface of the case;
      (3) an insulating material supporting the pin within the ferrule and in sealing engagement with the ferrule and with the pin;
      (4) a preformed electrically conductive block spaced from the ferrule by the insulating material, the block being in electrical connection with the pin; and
      (5) a device for electrical or electromagnetic protection having a first end and a second end and a flat portion therebetween which bridges across the spaced block and ferrule, the electrical or electromagnetic protection device being electrically connected at the first end to the ferrule and electrically connected at the second end to the block.

8. A medical device according to claim 7 wherein the conductive block is spaced from the ferrule by the insulating material.

9. A medical device according to claim 7 wherein the electrically conductive block has a flat top surface.

10. A medical device according to claim 9 also comprising an electrical circuit spaced apart from the conductive block and a conductor extending from the electrical circuit and electrically connected to the top of the conductive block.

11. A medical device according to claim 7, wherein the feedthrough is one of an array of similar feedthroughs, the array defining a linear axis, the electrical and electromagnetic protection devices being disposed at locations offset from the linear axis.

12. A medical device according to claim 7, wherein the device for electrical or electromagnetic protection comprises a chip capacitor.

* * * * *